United States Patent
Wang et al.

(10) Patent No.: US 11,051,680 B1
(45) Date of Patent: Jul. 6, 2021

(54) ENDOSCOPE STEREO IMAGING DEVICE

(71) Applicant: Industrial Technology Research Institute, Hsinchu (TW)

(72) Inventors: Chy-Lin Wang, Hsinchu County (TW); Yen-Chang Wang, Taoyuan (TW); Chih-Cheng Hsu, Miaoli County (TW); Hsiao-Yue Tsao, Hsinchu County (TW)

(73) Assignee: Industrial Technology Research Institute, Hsinchu (TW)

( * ) Notice: Subject to any disclaimer, the term of this patent is extended or adjusted under 35 U.S.C. 154(b) by 0 days.

(21) Appl. No.: 16/712,993

(22) Filed: Dec. 13, 2019

(30) Foreign Application Priority Data

Dec. 11, 2019 (TW) .................................. 108145270

(51) Int. Cl.
*A61B 1/00* (2006.01)
*H04N 5/225* (2006.01)
*A61B 1/06* (2006.01)
*H04N 13/239* (2018.01)

(52) U.S. Cl.
CPC ...... *A61B 1/00193* (2013.01); *A61B 1/00197* (2013.01); *A61B 1/0646* (2013.01); *H04N 5/2253* (2013.01); *H04N 5/2254* (2013.01); *H04N 13/239* (2018.05); *H04N 2005/2255* (2013.01)

(58) Field of Classification Search
None
See application file for complete search history.

(56) References Cited

U.S. PATENT DOCUMENTS

| 7,061,532 | B2 | 6/2006 | Silverstein | |
|---|---|---|---|---|
| 8,149,270 | B1 | 4/2012 | Yaron et al. | |
| 2014/0357951 | A1 | 12/2014 | Muller et al. | |
| 2017/0090177 | A1* | 3/2017 | Echigo | G06T 1/0007 |
| 2018/0007343 | A1* | 1/2018 | Send | G02F 1/29 |

FOREIGN PATENT DOCUMENTS

| CN | 103887708 | 6/2014 |
|---|---|---|
| CN | 104321005 | 1/2015 |
| CN | 103417181 | 12/2015 |

(Continued)

OTHER PUBLICATIONS

"Office Action of Taiwan Counterpart Application", dated May 14, 2020, p. 1-p. 7.

(Continued)

Primary Examiner — Heather R Jones
(74) Attorney, Agent, or Firm — JCIPRNET

(57) ABSTRACT

An endoscope stereo imaging device includes an endoscope lens assembly and an imaging module. The imaging module includes first, second and third lens assemblies, a beam splitter, first and second image sensors and a micro lens array. A light beam from the endoscope lens assembly is transmitted to the beam splitter after passing through the first lens assembly and is split into first and second portions of the light beam. The first portion light beam is transmitted to the first image sensor via the second lens assembly and forms a two-dimensional image. The second portion light beam is transmitted to the second image sensor via the third lens assembly and the micro lens array sequentially and forms a first three-dimensional image.

12 Claims, 12 Drawing Sheets

(56) References Cited

FOREIGN PATENT DOCUMENTS

| CN | 205181290 | 4/2016 |
|----|-----------|--------|
| CN | 104883555 | 1/2017 |
| JP | 2009031682 | 2/2009 |
| TW | 200503553 | 1/2005 |

OTHER PUBLICATIONS

Sam Y. Ba, et al., "4-mm-diameter three-dimensional imaging endoscope with steerable camera for minimally invasive surgery (3-D-Marvel)." Neurophotonics, vol. 4, No. 1, Jan.-Mar. 2017. pp. 1-8.

Kurtis Keller, et al., "A single-imager stereoscopic endoscope." Proceedings of SPIE, vol. 7964, Mar. 1, 2011, pp. 1-7.

Steven Yi, et al., "Augmenting Endoscopic Instruments with 3D Surface Imaging." Proceedings of SPIE, vol. 10868, Feb. 26, 2019, pp. 1-7.

Takaomi Sekiya, et al., "Development of a dual-view endoscope system." Proceedings of SPIE, vol. 6080, Feb. 25, 2006, pp. 1-11.

Tuqiang Xie, et al., "Grin lens rod based probe for endoscopic spectral domain optical coherence tomography with fast dynamic focus tracking." Optics Express, vol. 14, No. 8, Apr. 17, 2006, pp. 3238-3246.

Patrik Langehanenberg, et al., "High precision geometrical characterization and alignment of miniaturized optics." Proceedings of SPIE, vol. 8249, Feb. 14, 2012, pp. 1-7.

Manhong Chan, et al., "Miniaturized 3D Endoscopic Imaging System." Proceedings of SPIE, vol. 4958, Jul. 22, 2003, pp. 1-6.

Dewen Cheng, et al., "Optical design and evaluation of a 4 mm cost-effective ultra-high-definition arthroscope." Biomedical Optics Express, vol. 5, No. 8, Aug. 1, 2014, pp. 2697-2714.

Yi Qin, et al., "Optical design and system engineering of a multiresolution foveated laparoscope." Applied Optics, vol. 55, No. 11, Apr. 10, 2016, pp. 3058-3068.

S. A. Boppart, et al., "Optical imaging technology in minimally invasive surgery." Surgical Endoscopy, vol. 13, Jul. 1999, pp. 718-722.

Vladislav Batshev, et al., "Stereoscopic tip for a video endoscope: problems in design." Proceedings of SPIE, vol. 10466, Nov. 30, 2017, pp. 1-5.

\* cited by examiner

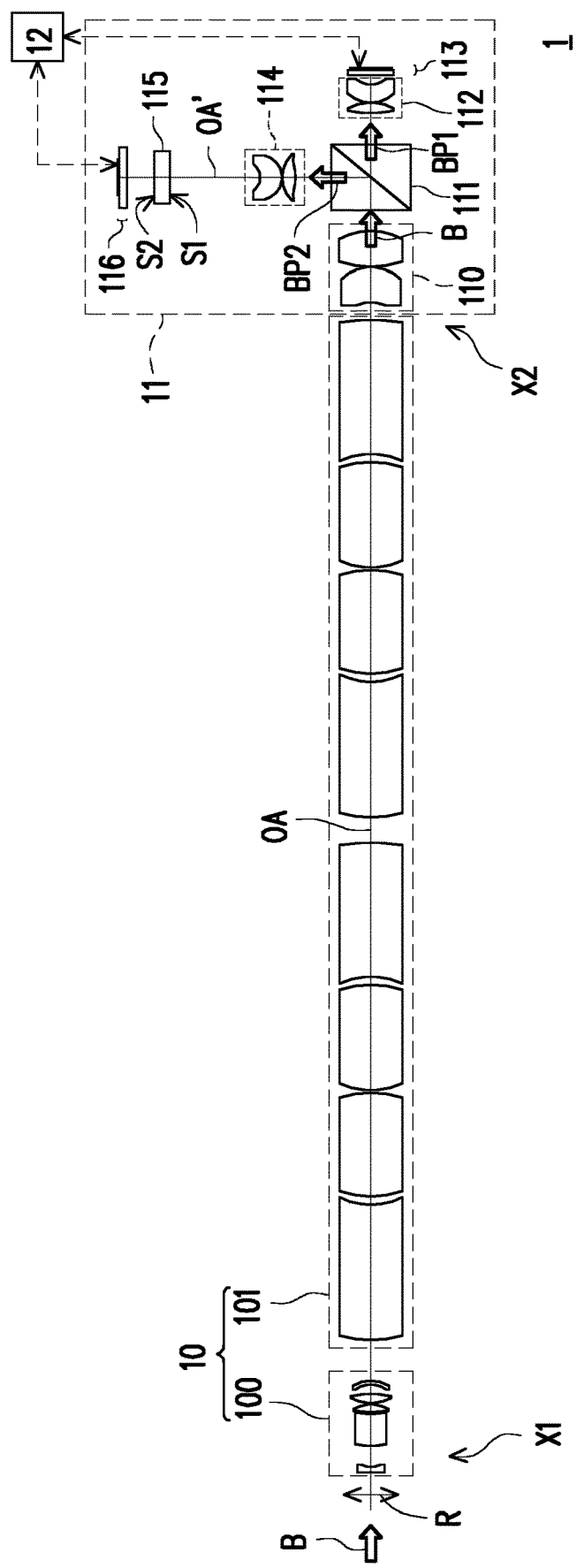
[FIG. 1]

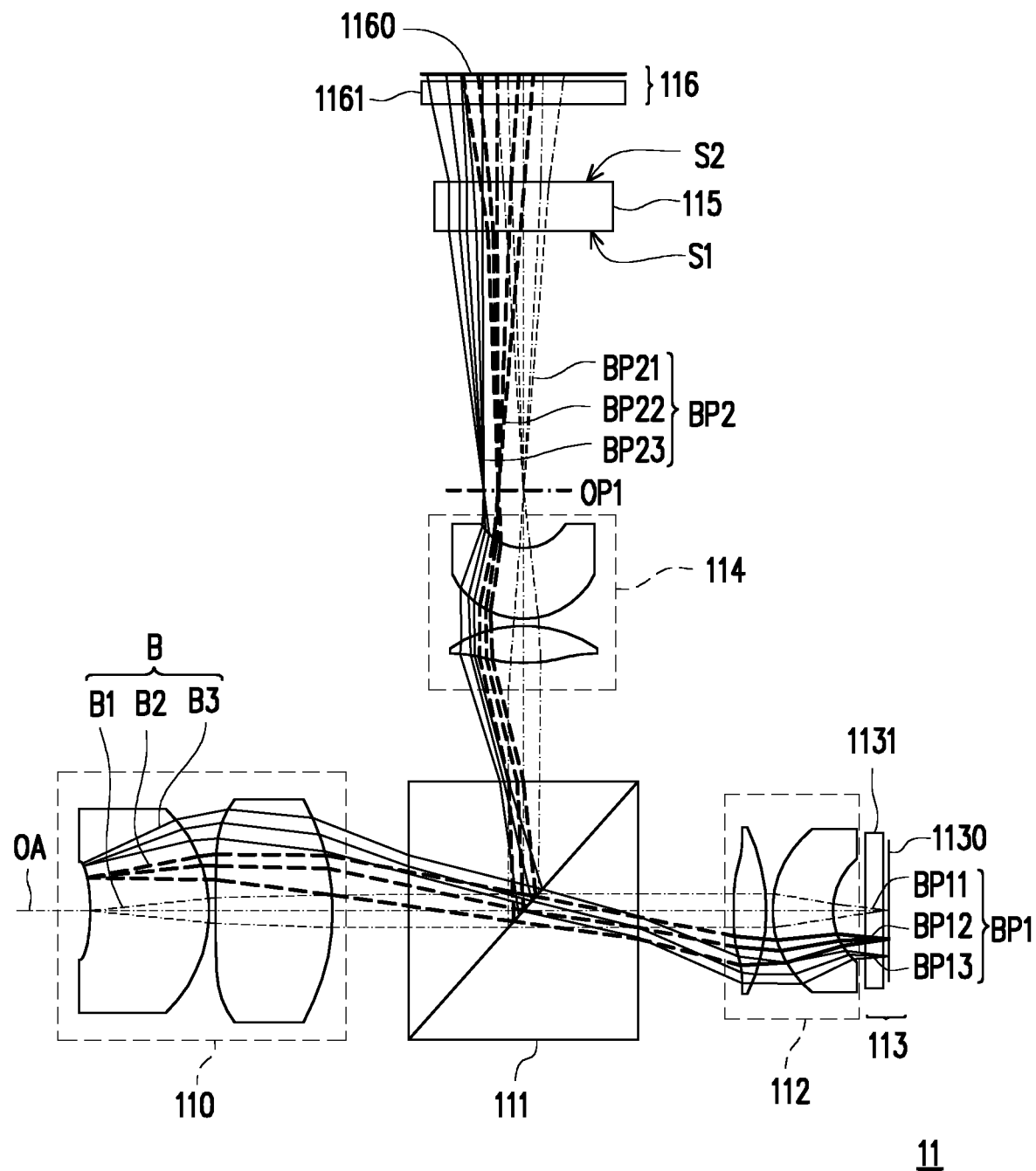
【FIG. 2】

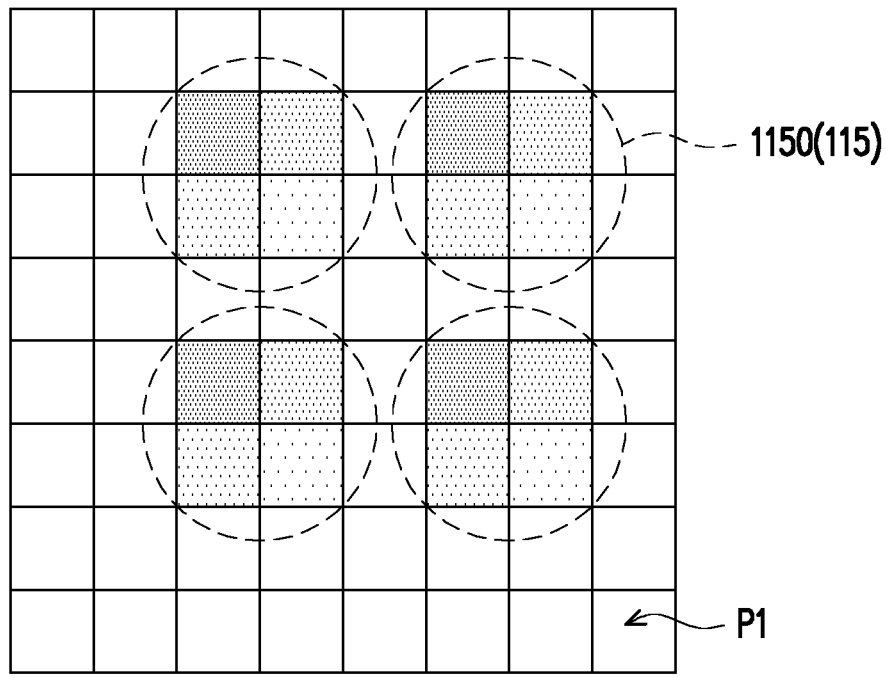
【FIG. 3】
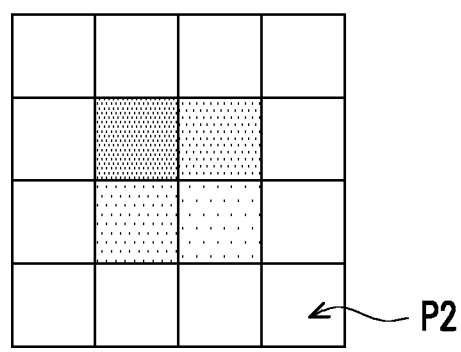
【FIG. 4】

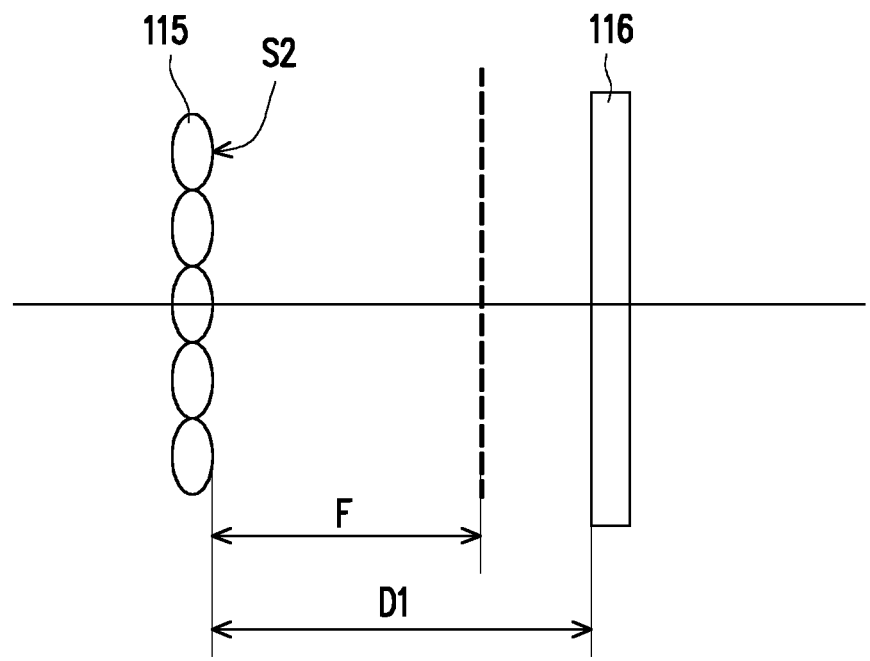
【FIG. 5】
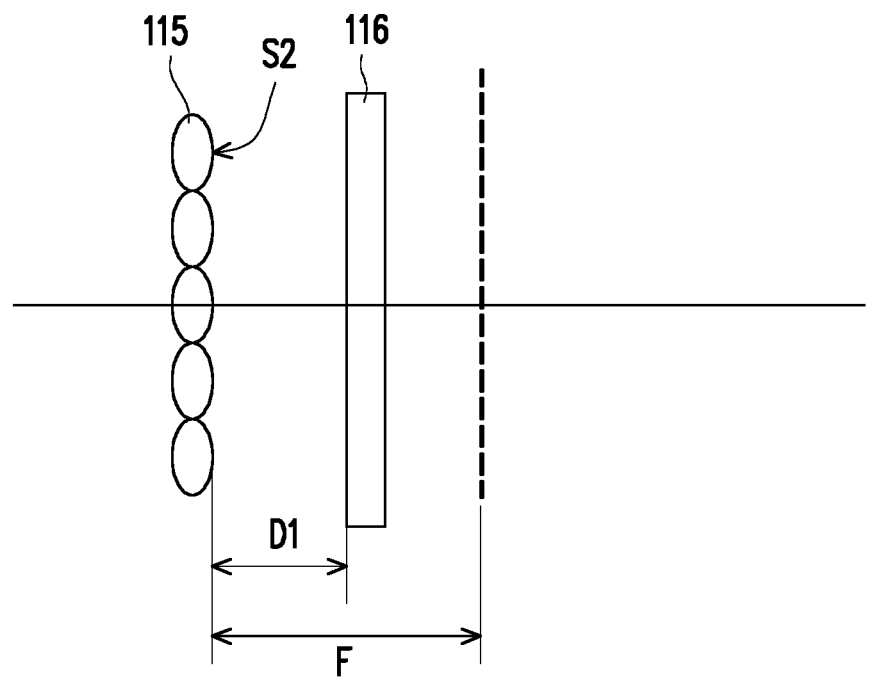
【FIG. 6】

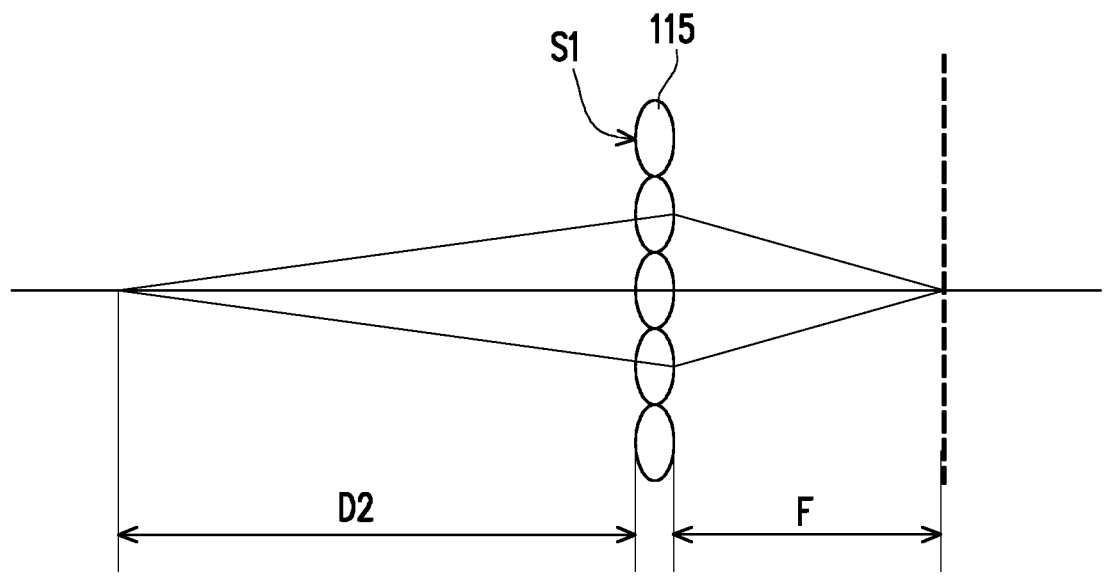
【FIG. 7】
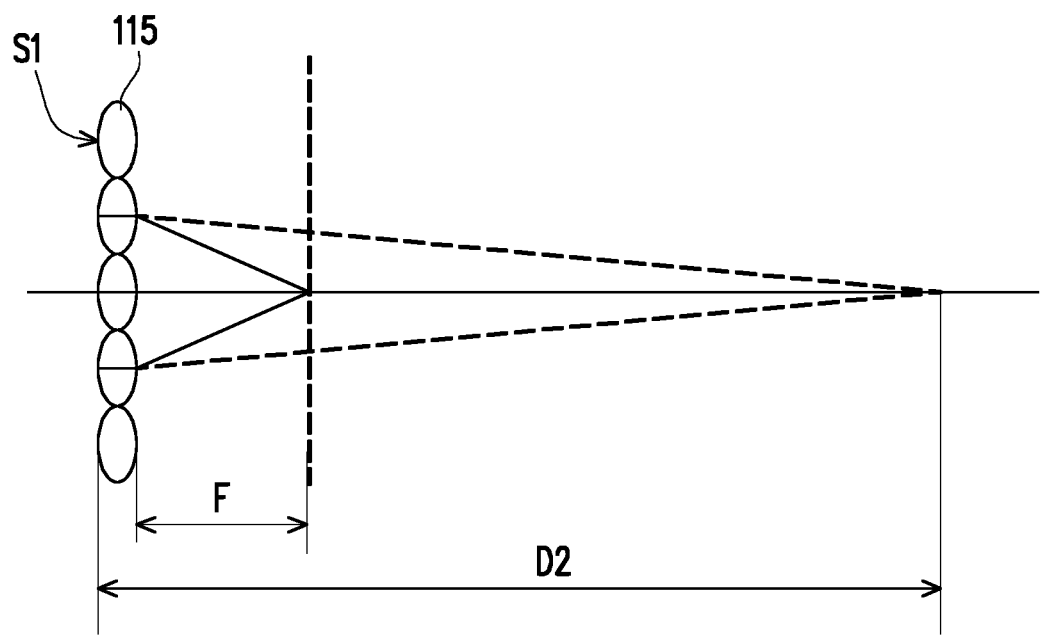
【FIG. 8】

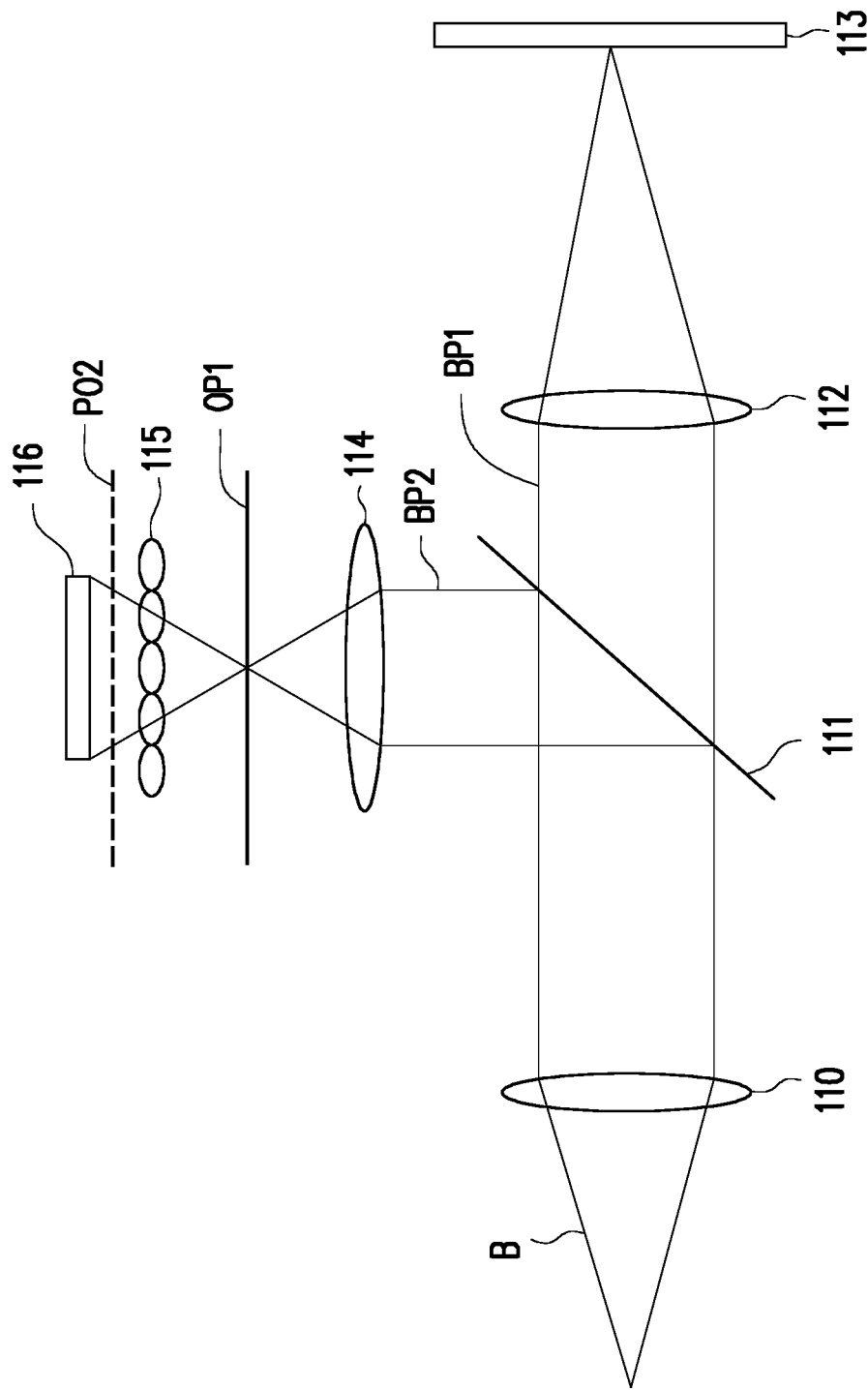

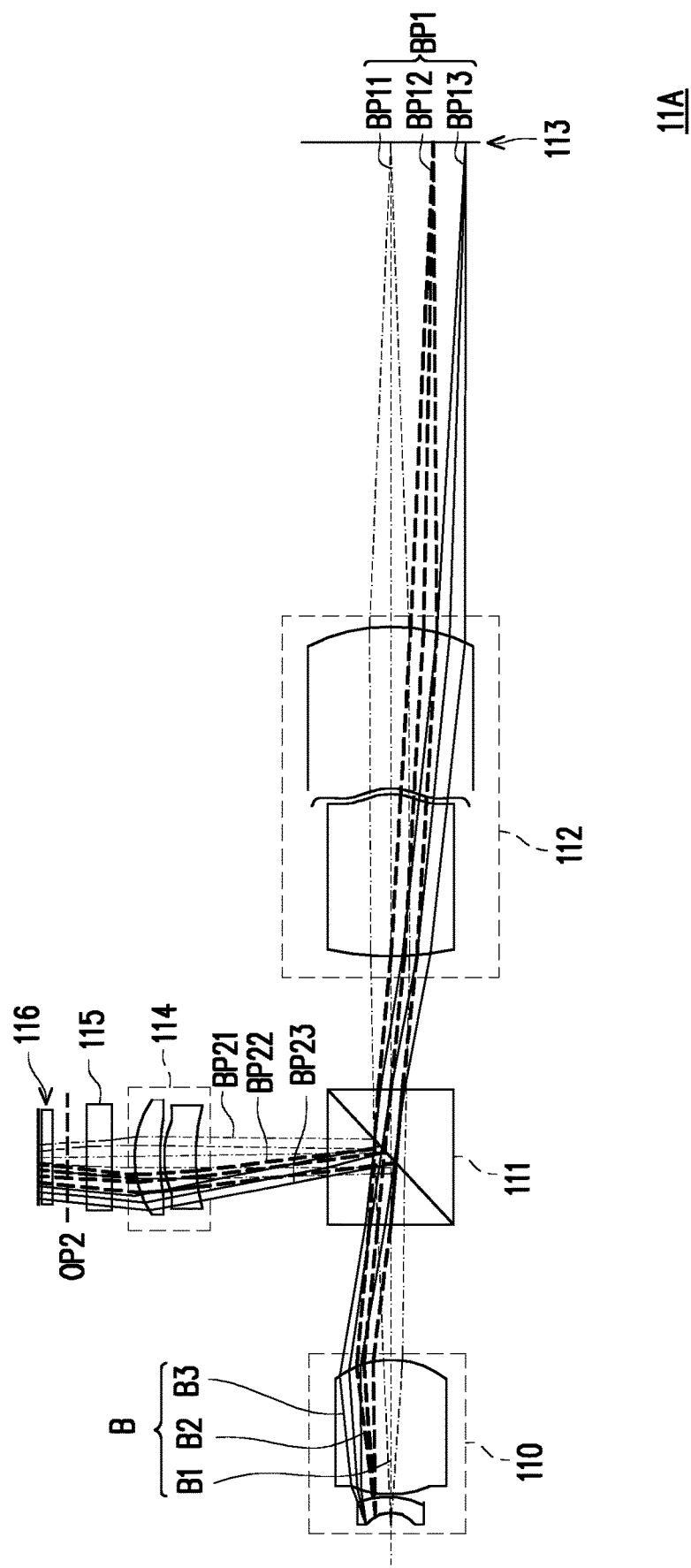
[FIG.10]

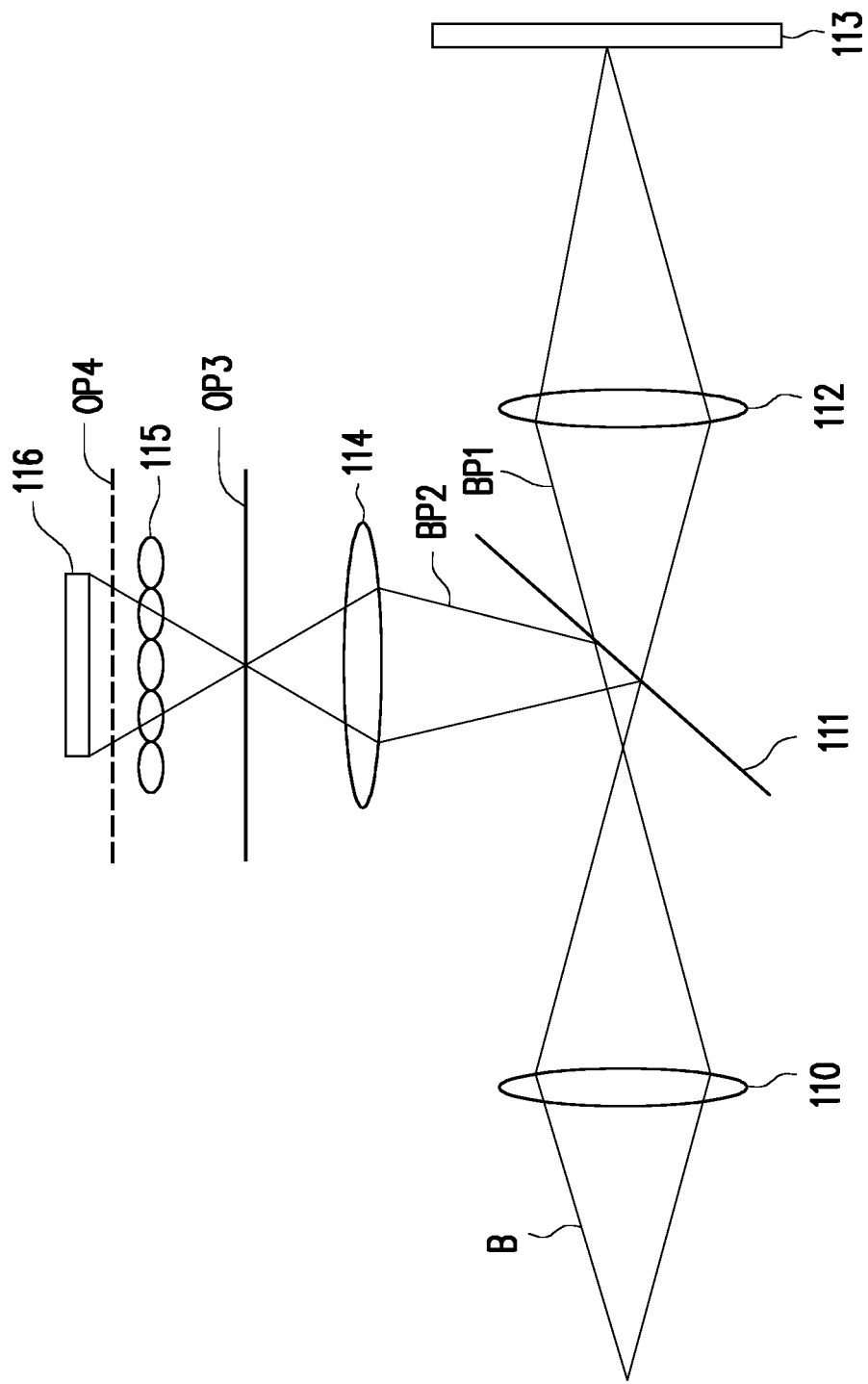
[FIG.11]

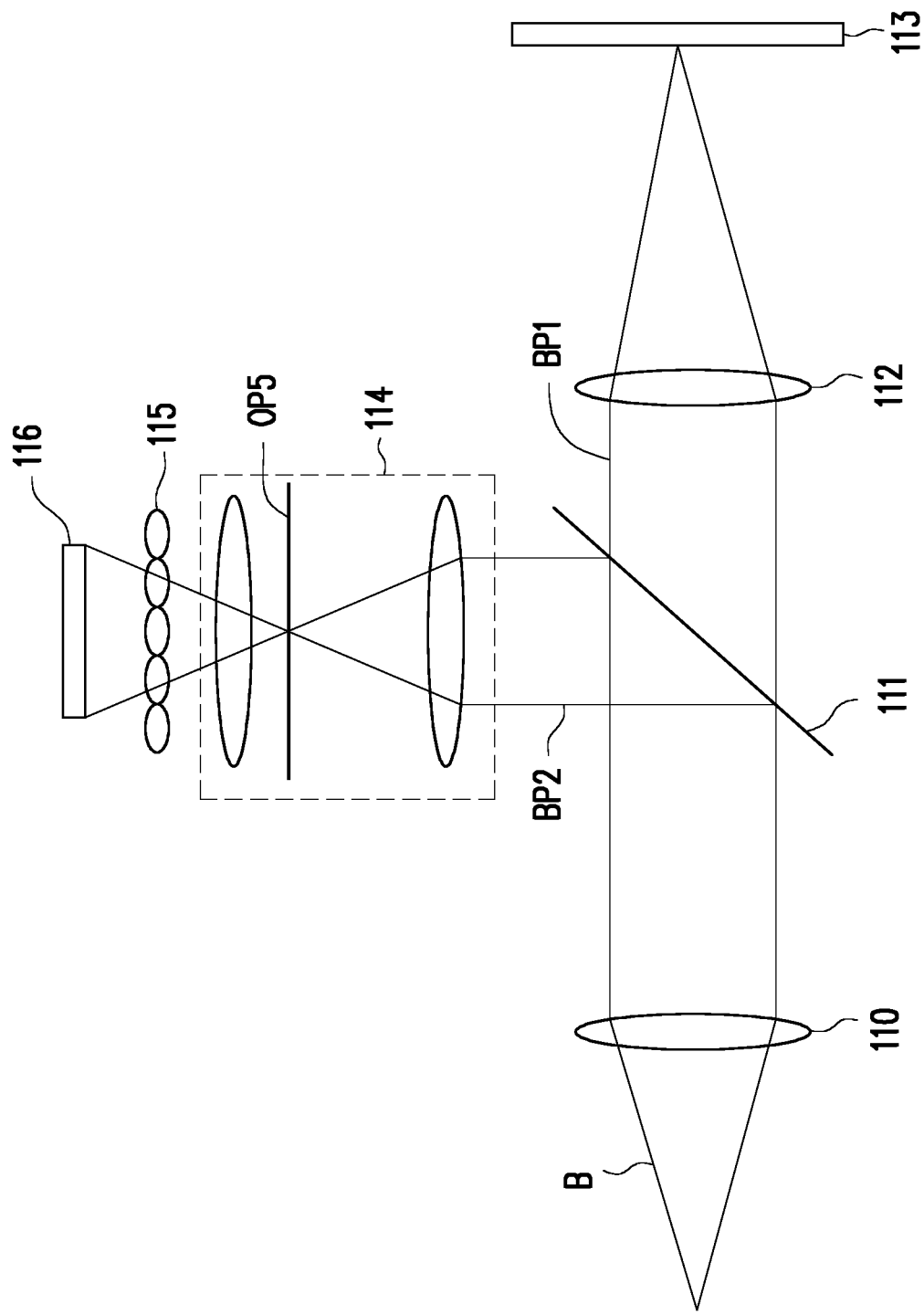

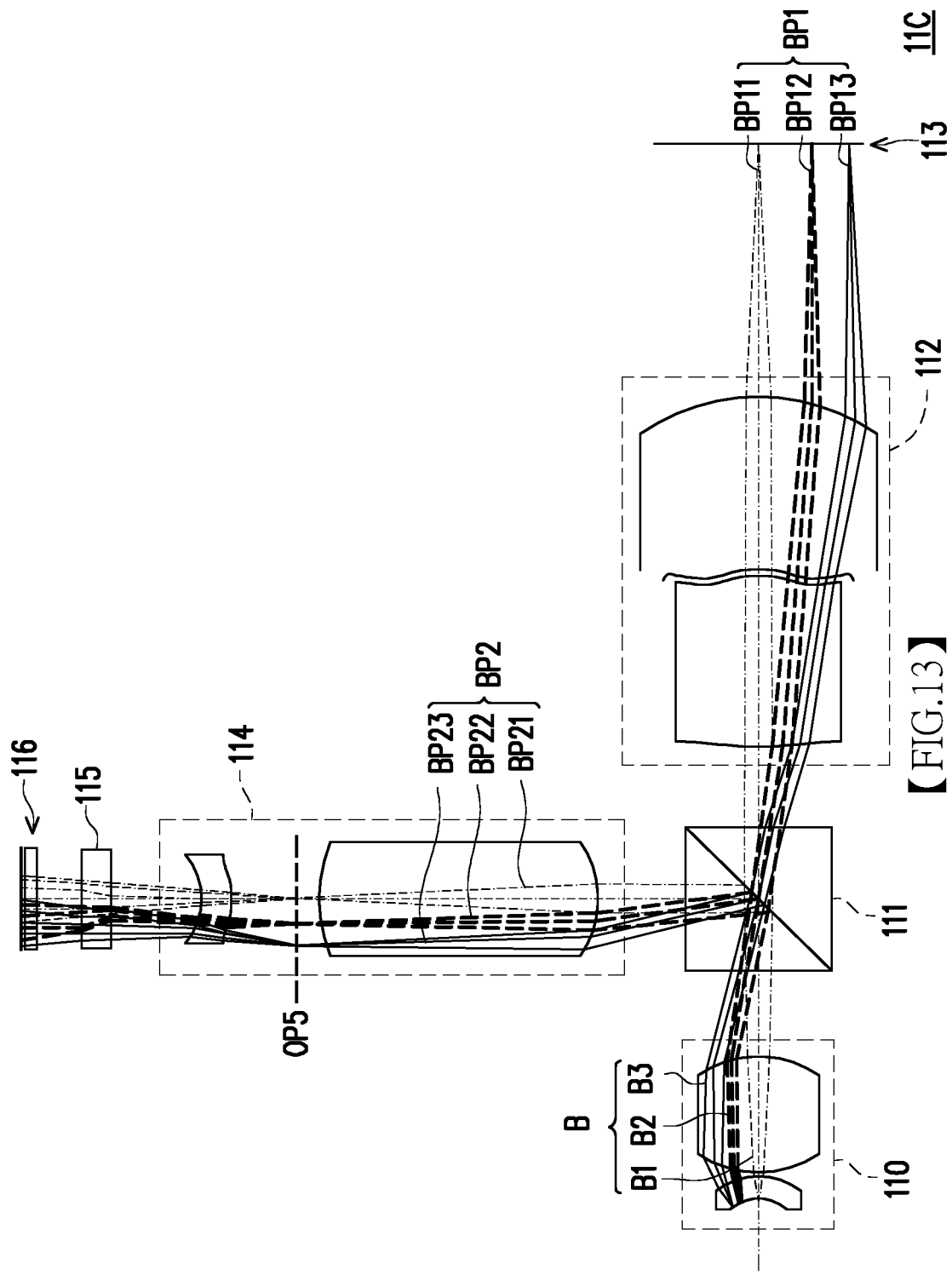
[FIG.13]

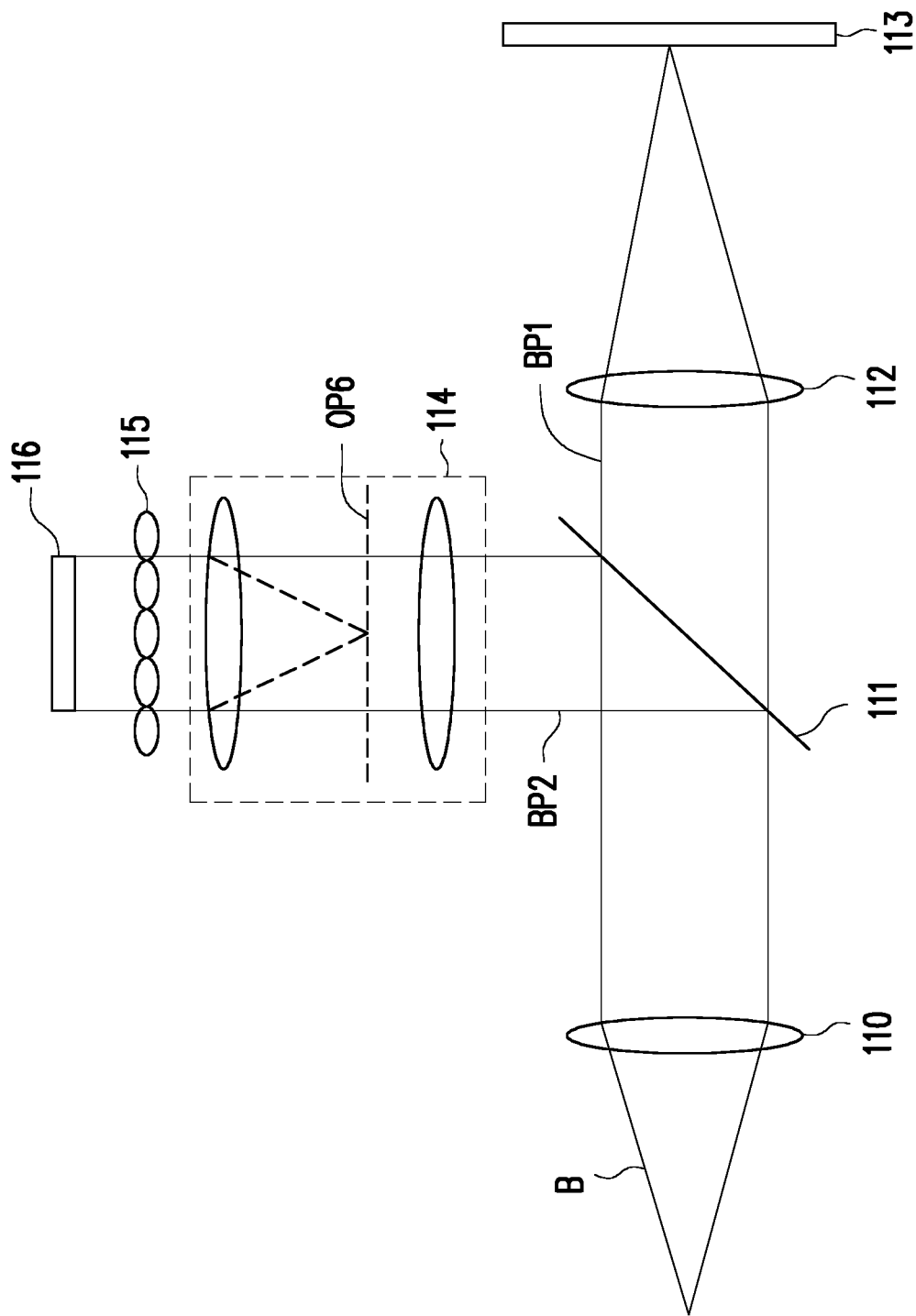
[FIG. 14]

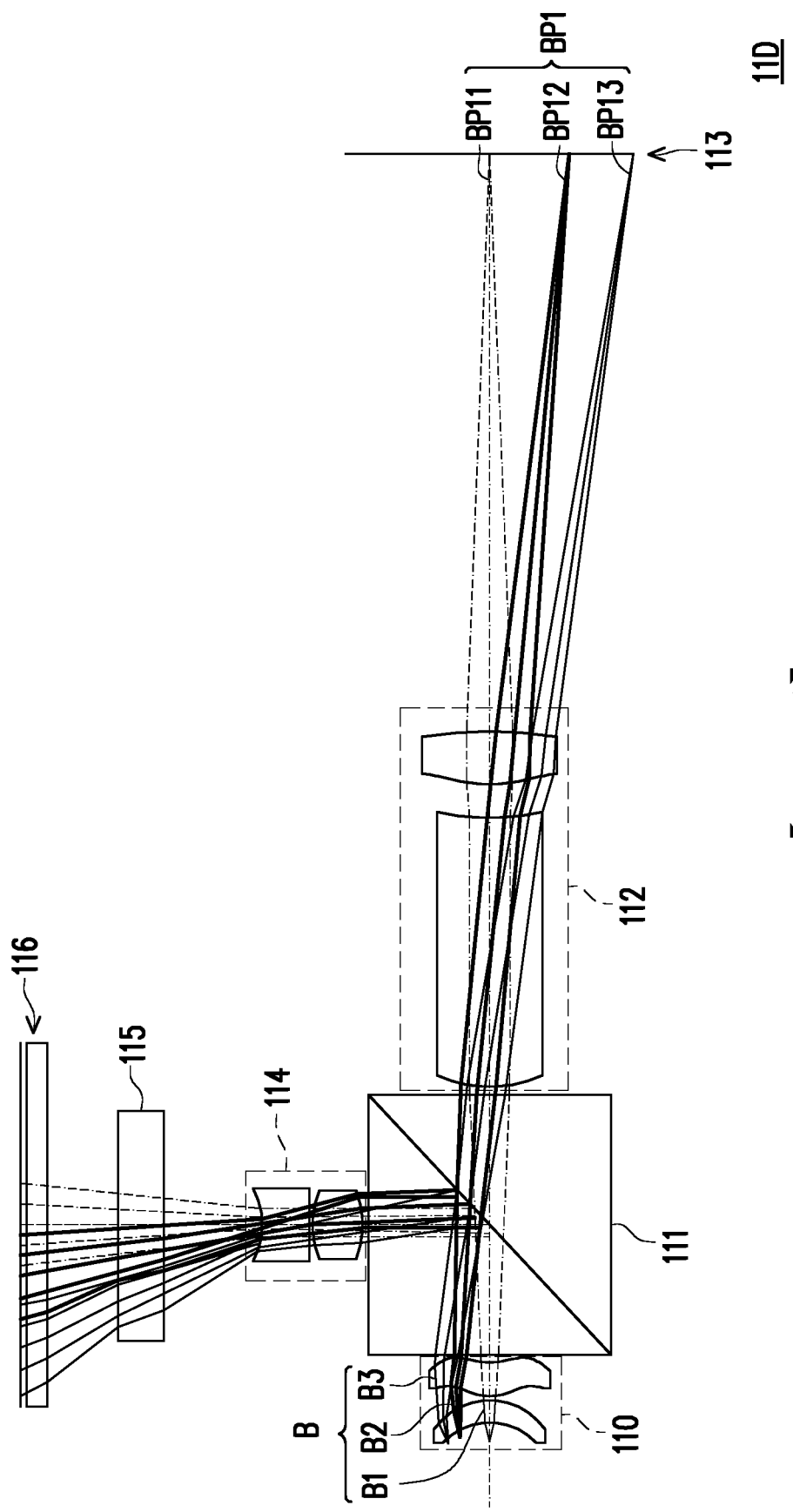
[FIG. 15]

ENDOSCOPE STEREO IMAGING DEVICE

CROSS-REFERENCE TO RELATED APPLICATION

This application claims the priority benefit of Taiwan application serial no. 108145270, filed on Dec. 11, 2019. The entirety of the above-mentioned patent application is hereby incorporated by reference herein and made a part of this specification.

TECHNICAL FIELD

The disclosure relates to an endoscope and more particularly, to an endsoscope stereo imaging device.

BACKGROUND

In recent years, "minimally invasive surgeries" as having advantages, such as small wounds and short recovery time, have become a trend. Most of the minimally invasive surgeries are performed by using a two-dimensional (2D) photography technique. A surgeon can perform the surgery by using a 2D image transmitted onto a screen via an endoscope. Because the 2D image lacks of depth information, there is difficulty existing in the treatment of delicate surgery during the minimally invasive surgery performed by using the 2D photography technique. In order to overcome technical issues caused by the 2D photography technique, a three-dimensional (3D) photography technique has been subsequently developed. As a 3D image is capable of presenting depth and distance information, the surgeon can accomplish spatially positioning more accurately when performing the fine surgery, so as to improve surgery accuracy, shorten an operation duration and reduce the risk of surgery.

However, a currently available 3D endoscope is composed of dual endoscopes to form a 3D image by capturing images at two different view angles using two endoscope assemblies. As the two different view angles must be fixed, i.e., a configuration relation between the two endoscope assemblies must be fixed, it is difficult for the currently available 3D endoscope to achieve diameter miniaturization.

SUMMARY

An endoscope stereo imaging device is introduced by the embodiments of the disclosure, which is potential for miniaturization of an endoscope diameter.

An endoscope stereo imaging device of the embodiments of the disclosure includes an endoscope lens assembly and an imaging module. The endoscope lens assembly is configured to receive and transmit a light beam. The imaging module is disposed on a transmission path of the light beam and includes a first lens assembly, a beam splitter, a second lens assembly, a first image sensor, a third lens assembly, a micro lens array and a second image sensor. The light beam from the endoscope lens assembly is transmitted to the beam splitter after passing through the first lens assembly and is split into a first portion and a second portion light beams. The first portion light beam is transmitted to the first image sensor via the second lens assembly and forms a two-dimensional image. The second portion light beam is transmitted to the second image sensor via the third lens assembly and the micro lens array sequentially and forms a first three-dimensional image.

Several exemplary embodiments accompanied with figures are described in detail below to further describe the disclosure in details.

BRIEF DESCRIPTION OF THE DRAWINGS

The accompanying drawings are included to provide a further understanding of the disclosure, and are incorporated in and constitute a part of this specification. The drawings illustrate embodiments of the disclosure and, together with the description, serve to explain the principles of the disclosure.

FIG. 1 is a schematic view of an endoscope stereo imaging device according to an embodiment of the disclosure.

FIG. 2 is a schematic enlarged view of the imaging module depicted in FIG. 1.

FIG. 3 and FIG. 4 are schematic views of a two-dimensional image and a three-dimensional image, respectively, for explaining why a spatial resolution of the three-dimensional image is reduced.

FIG. 5 and FIG. 6 are schematic views respectively illustrating two types of relative relationships among the micro lens array, an effective focal length of the micro lens array and the second image sensor.

FIG. 7 and FIG. 8 are schematic views respectively illustrating two types of relative relationships between the object plane of the micro lens array and the effective focal length of the micro lens array.

FIG. 9 is a schematic view of an imaging module according to a first embodiment of the disclosure.

FIG. 10 is a schematic view of an example of the imaging module depicted in FIG. 9.

FIG. 11 is a schematic view of an imaging module according to a second embodiment of the disclosure.

FIG. 12 is a schematic view of an imaging module according to a third embodiment of the disclosure.

FIG. 13 is a schematic view of an example of the imaging module depicted in FIG. 12.

FIG. 14 is a schematic view of an imaging module according to a fourth embodiment of the disclosure.

FIG. 15 is a schematic view of an example of the imaging module depicted in FIG. 14.

DESCRIPTION OF EMBODIMENTS

In the following embodiments, wordings used to indicate directions, such as "up," "down," "front," "back," "left," and "right", merely refer to directions in the accompanying drawings. Thus, the language is used for the directions, but not intended to limit the scope of the disclosure.

In the accompanying drawings, the drawings illustrate the general features of the methods, structures, and/or materials used in the particular exemplary embodiments. However, these drawings should not be construed as defining or limiting the scope or nature of what is covered by these exemplary embodiments. For example, the relative size, thickness and location of each film layer, region or structure may be reduced or enlarged for clarity.

In the embodiments, the same or similar elements will be designated by the same or similar reference numerals, and descriptions thereof will be omitted. In addition, the features of different exemplary embodiments may be combined with each other when they are not in conflict, and simple equivalent changes and modifications made according to the specification or the claims are still within the scope of the disclosure.

Terms such as "first" and "second" mentioned throughout the specification or the claims of this application are only for naming the names of the elements or distinguishing different embodiments or scopes and are not intended to limit the upper limit or the lower limit of the number of the elements nor intended to limit manufacturing sequences or disposition sequences of the elements.

FIG. 1 is a schematic view of an endoscope stereo imaging device 1 according to an embodiment of the disclosure. Referring to FIG. 1, the endoscope stereo imaging device 1 includes an endoscope lens assembly 10 configured to receive and transmit a light beam B, an imaging module 11 disposed on a transmission path of the light beam B from the endoscope lens assembly 10 and a processor 12 coupled to the imaging module 11.

The endoscope lens assembly 10 presents a strip shape and has a first terminal X1 and a second terminal X2, wherein the second terminal X2 is opposite to the first terminal X1 and located between the first terminal X1 and the imaging module 11. In practical operation, the first terminal X1 may be disposed adjacent to a test object (not shown) to receive a light beam (e.g., the light beam B) reflected by the test object, so as to obtain an image of the test object. The test object may be an organ or a tissue to be processed, or may be a lesion location or a related nerve, blood vessel or tissue therearound.

In some embodiments, the endoscope lens assembly 10 may include an objective lens assembly 100 and a relay lens assembly 101 configured for image extending. The objective lens assembly 100 and the relay lens assembly 101 are arranged in sequence from the first terminal X1 and the second terminal X2 along an optical axis OA of the endoscope lens assembly 10. In some embodiments, each of the objective lens assembly 100 and the relay lens assembly 101 includes one or more lens elements, and a composition and an optical parameter design of each of the objective lens assembly 100 and the relay lens assembly 101 are not particularly limited herein. In other embodiments, the relay lens assembly 101 may be omitted from the endoscope lens assembly 10.

The imaging module 11 receives the light beam B from the endoscope lens assembly 10 and accordingly forms an image. In some embodiments, the imaging module 11 may include a first lens assembly 110, a beam splitter 111 disposed on the transmission path of the light beam B from the first lens assembly 110, a second lens assembly 112 disposed on a transmission path of a light beam (e.g., a first portion light beam BP1) from the beam splitter 111, a first image sensor 113 disposed on a transmission path of a light beam (e.g., the first portion light beam BP1) from the second lens assembly 112, a third lens assembly 114 disposed on a transmission path of a light beam (e.g., a second portion light beam BP2) from the beam splitter 111, a micro lens array 115 disposed on a transmission path of a light beam (e.g., the second portion light beam BP2) from the third lens assembly 114 and a second image sensor 116 disposed on a transmission path of a light beam (e.g., the second portion light beam BP2) from the micro lens array 115.

FIG. 2 is a schematic enlarged view of the imaging module 11 depicted in FIG. 1. FIG. 2 further illustrates three types of light beams (represented by light beams B1, B2 and B3) having three different fields of view of the light beam B depicted in FIG. 1. Three types of light beams (represented by first portion light beams BP11, BP12 and BP13) having different fields of views of the first portion light beam BP1 depicted in FIG. 1 and three types of light beams (represented by second portion light beams BP21, BP22 and BP23) having different fields of views of the second portion light beam BP2 depicted in FIG. 1, wherein the first portion light beam BP11 and the second portion light beam BP21 are from the light beam B1, the first portion light beam BP12 and the second portion light beam BP22 are from the light beam B2, and the first portion light beam BP13 and the second portion light beam BP23 are from the light beam B3.

Referring to FIG. 1 and FIG. 2, the light beam B (including the light beams B1, B2 and B3), after entering the endoscope lens assembly 10, passes through the objective lens assembly 100 and the relay lens assembly 101 and is transmitted to the imaging module 11. The light beam B (including the light beams B1, B2 and B3) from the endoscope lens assembly 10 passes through the objective lens assembly 100 and enters the imaging module 11. In some embodiments, the first lens assembly 110 and the endoscope lens assembly 10 may be designed to be optically coaxial. In some embodiments, the first lens assembly 110 may include one or more lens elements, and a composition and an optical parameter design of the first lens assembly 110 are not particularly limited herein.

The light beam B (including the light beams B1, B2 and B3) from the endoscope lens assembly 10, after passing through the first lens assembly 110, is transmitted to the beam splitter 111 and is split by the beam splitter 111 into the first portion light beam BP1 (including the first portion light beams BP11, BP12 and BP13) and the second portion light beam BP2 (including the first portion light beams BP21, BP22 and BP23). In some embodiments, the beam splitter 111 may include a beam splitter prism, a beam splitter lens or other adaptive beam splitter elements. Moreover, the beam splitter 111 may split the light according to a wavelength or energy. In a scenario that the light is split according to the energy, a splitting ratio may vary according to a demand and is not limited to 50% of each. In some embodiments, the beam splitter 111 allows the first portion light beam BP1 to pass through and reflects the second portion light beam BP2. In other embodiments, the beam splitter 111 allows the second portion light beam BP2 to pass through and reflects the first portion light beam BP1.

The first portion beam BP1 is transmitted to the first image sensor 113 via the second lens assembly 112 and forms a two-dimensional image (not shown). In some embodiments, the second lens assembly 112 may include one or more lens elements, and a composition and an optical parameter design of the second lens assembly 112 are not particularly limited herein. In some embodiments, the first image sensor 113 may include a charge coupled device (CCD), a complementary metal oxide semiconductor (CMOS) or another adaptive sensing element 1130. In some embodiments, the first image sensor 113 may further include a transparent protective cover 1131 (referring to FIG. 2). The transparent protective cover 1131 may be disposed between the second lens assembly 112 and the sensing element 1130 to protect the sensing element 1130 (from, for example, scratches or dust).

The second portion beam BP2 is transmitted to the second image sensor 116 via the third lens assembly 114 and the micro lens array 115 sequentially. As illustrated in FIG. 2, the micro lens array 115 may disperse the light beams (e.g., the second portion light beams BP21, BP22 and BP23) at respective fields of view into a plurality of sub light beams. The sub light beams respectively form images at different locations of the second image sensor 116 to form a first three-dimensional image.

In some embodiments, the third lens assembly 114 may include one or more lens elements, and a composition and an optical parameter design of the third lens assembly 114 are not particularly limited herein. In some embodiments, one of an object side surface S1 and an image side surface S2 of the micro lens array 115 is a convex micro lens array surface. In other words, at least one of the object side surface S1 and the image side surface S2 includes a plurality of convex micro lenses 1150 (referring to FIG. 3), and these micro lenses 1150 are arranged in an array. In some embodiments, the second image sensor 116 may include a CCD, a CMOS or another adaptive sensing element 1160. In some embodiments, the second image sensor 116 may further include a transparent protective cover 1161. The transparent protective cover 1161 may be disposed between the third lens assembly 114 and the sensing element 1160 to protect the sensing element 1160 (from, for example, scratches or dust).

As illustrated in FIG. 1, in some embodiments, the second lens assembly 112, the first lens assembly 110, the objective lens assembly 100 and the relay lens assembly 101 may be designed to be optically coaxial, and the third lens assembly 114 and the micro lens array 115 may be designed to be optically coaxial, wherein an optical axis OA' of the third lens assembly 114 and the micro lens array 115 may be perpendicular to the optical axis OA, but the disclosure is not limited thereto. In other embodiments, the second lens assembly 112 and the first image sensor 113 may be exchanged with the third lens assembly 114, the micro lens array 115 and the second image sensor 116, i.e., the third lens assembly 114, the micro lens array 115, the first lens assembly 110, the objective lens assembly 100 and the relay lens assembly 101 may be designed to be optically coaxial.

FIG. 3 and FIG. 4 are schematic views respectively illustrating a two-dimensional image IM1 and the three-dimensional image IM2 for explaining why a spatial resolution of the three-dimensional image IM2 is reduced. In FIG. 3, multiple (e.g., four) background colors are used respectively to represent pixels P1 where light beams having multiple (e.g., four) fields of view are projected. The light beams (e.g., the second portion light beams BP21, BP22 and BP23) at respective fields of view as illustrated in FIG. 2 are dispersed into a plurality of sub light beams by the micro lens array 115, these sub light beams are respectively projected to N (e.g., four) pixels P1 (referring to FIG. 3) in the second image sensor 116, and these N (e.g., four) pixels P1 correspond to different locations of different micro lenses 1150. Each pixel P2 of the three-dimensional image IM2 illustrated in FIG. 4 is formed by combining N (e.g., four) pixels P1 having the same background color of the two-dimensional image as illustrated in FIG. 3, and thus, a resolution of the reconstructed three-dimensional image IM2 (i.e., the first three-dimensional image generated by the second image sensor 116 illustrated in FIG. 1 and FIG. 2) is 1/N of a resolution of the two-dimensional image generated by the first image sensor 113. Taking a scenario that N=4 in FIG. 3 and FIG. 4 as an example for explanation, N may be any other integer greater than 1. As the value of N is increased, the spatial resolution of the three-dimensional image IM2 reduced. That is, the less clear the image is, the more likely it causes a misjudgment.

In order to improve the issue that the spatial resolution of the three-dimensional image is low, referring to FIG. 1, the processor 12 is coupled to the first image sensor 113 and the second image sensor 116. The coupling may refer to signal transmission in a wired or a wireless manner. The processor 12 may generate a second three-dimensional image according to the two-dimensional image (the image generated by the first image sensor 113) and the first three-dimensional image (the image generated by the second image sensor 116), and a resolution of the second three-dimensional image may be higher than the resolution of the first three-dimensional image. Specifically, the processor 12 may compare the two-dimensional image and the first three-dimensional image and compensate insufficient pixels by an algorithm, for example, by compensating information missing in the 3D image using the 2D image, so as to enhance the resolution of the 3D image. In some embodiments, the resolution of the second three-dimensional image may be equal to the resolution of the two-dimensional image (the image generated by the first image sensor 113).

In some embodiments, the processor 12 may include an arithmetic logic unit, a control unit, a memory unit or other required units. For example, the arithmetic logic unit, the control unit and the memory unit may be a central processing unit (CPU), a controller and a temporary memory, respectively, but the disclosure is not limited thereto.

Light beams having various fields of view are received by using the micro lens array 115 to reconstruct the 3D image (the first three-dimensional image generated by the second image sensor 116), and a resolution of the reconstructed 3D image is enhanced by using the 2D image generated by the first image sensor 113, such that the 3D image (the second three-dimensional image) having a higher resolution is obtained. The 3D image which may be formed without using dual endoscope lens assemblies is potential for miniaturization of the endoscope diameter R (referring to FIG. 1). Moreover, as the 3D image is capable of presenting depth and distance information, a surgeon, when performing a fine surgery, is able to perform spatially positioning more accurately, so as to improve surgery accuracy, shorten an operation duration and reduce the risk of surgery.

FIG. 5 and FIG. 6 are schematic views respectively illustrating two types of relative relationships among the micro lens array 115, an effective focal length F of the micro lens array 115 and the second image sensor 116. In FIG. 5 and FIG. 6, D1 is a distance between a most convex point of the image side surface S2 of the micro lens array 115 and the second image sensor 116, and F is an effective focal length (EFL) of the micro lens array 115.

As illustrated in FIG. 5, if the endoscope stereo imaging device meets $1.21F<D1<1.5F$, an object plane of the micro lens array 115 is a real image and an image plane of the micro lens array 115 renders a real image on the second image sensor 116. The real image has an ideal optical resolution and aberration and thus, is sufficient for subsequent image processing. As illustrated in FIG. 6, if the endoscope stereo imaging device meets $0.4F<D1<0.84F$, the object plane of the micro lens array 115 is a virtual image and the image plane of the micro lens array 115 renders a real image on the second image sensor 116. The real image has an ideal optical resolution and aberration and thus, is sufficient for subsequent image processing. In the structures illustrated in FIG. 5 and FIG. 6, if the distance D1 is less than a lower limit of the relational formula, an optical resolution may be insufficient; and if the distance D1 is more than an upper limit of the relational formula, the image becomes less clear due to too large aberration. Moreover, in the structure that the object plane of the micro lens array 115 is the real image, a higher brightness uniformity may be obtained, while in the structure that the object plane of the micro lens array 115 is the virtual image, a higher optical resolution or higher clarity may be obtained.

FIG. 7 and FIG. 8 are schematic views respectively illustrating two types of relative relationships between the object plane of the micro lens array 115 and the effective focal length of the micro lens array 115. In FIG. 7 and FIG.

8, D2 is a distance between the object plane of the micro lens array 115 and a most convex point of the object side surface S1 of the micro lens array 115. Taking a traveling direction of a light path which is from left to right as an example, a negative value of the distance D2 represents that the object plane of the micro lens array 115 is at the left of the micro lens array 115, while a positive value of the distance D2 represents that the object plane of the micro lens array 115 is at the right of the micro lens array 115.

As illustrated in FIG. 7, if the endoscope stereo imaging device meets −8.78F<D2<−3.76F, the object plane of the micro lens array 115 is a real image and located at the left of the micro lens array 115. As illustrated in FIG. 8, if the endoscope stereo imaging device meets 0.75F<D2<5.03F, the object plane of the micro lens array 115 is a virtual image and located at the right of the micro lens array 115. In the structures illustrated in FIG. 7 and FIG. 8, if the distance D2 is less than a lower limit of the relational formula, an optical resolution of the real image on the second image sensor 116 is insufficient; and if the distance D2 is more than an upper limit of the relational formula, and the real image of the second image sensor 116 becomes less clear due to too large aberration. Moreover, in the structure that the object plane of the micro lens array 115 is the real image, a higher brightness uniformity may be obtained, while in the structure that the object plane of the micro lens array 115 is the virtual image, a higher optical resolution or clarity may be obtained.

FIG. 9 is a schematic view of an imaging module 11A according to a first embodiment of the disclosure. FIG. 10 is a schematic view of an example of the imaging module 11A depicted in FIG. 9. Referring to FIG. 9, in some embodiments, as illustrated in FIG. 2, an object plane (represented as an object place OP1, for example) of the micro lens array 115 may be located between the third lens assembly 114 and the micro lens array 115. In other embodiments, as illustrated in FIG. 10, an object plane (represented as an object place OP2, for example) of the micro lens array 115 may be located at any location at a side of the micro lens array 115 which is far away from the third lens assembly 114.

FIG. 11 is a schematic view of an imaging module 11B according to a second embodiment of the disclosure. Referring to FIG. 11, the light beam B from the first lens assembly 110 may form a real image between the first lens assembly 110 and the second lens assembly 112 (or between the first lens assembly 110 and the third lens assembly 114) and then, form a real image via the second lens assembly 112 or the third lens assembly 114 (for example, form a real image at the location where an object plane OP3 is located). In some embodiments, the object plane (represented as the object place OP3, for example) of the micro lens array 115 may be located between the third lens assembly 114 and the micro lens array 115. In other embodiments, an object plane (represent as an object place OP4, for example) of the micro lens array 115 may be located at any location at a side of the micro lens array 115 which is far away from the third lens assembly 114.

FIG. 12 is a schematic view of an imaging module 11C according to a third embodiment of the disclosure. FIG. 13 is a schematic view of an example of the imaging module 11C depicted in FIG. 12. Referring to FIG. 12 and FIG. 13, an object plane (represented as an object place OP5, for example) of the micro lens array 115 may be located in the third lens assembly 114, and the second portion light beam BP2 may form a real image on the object plane (represented as an object place OP5, for example) of the micro lens array 115. In detail, the third lens assembly 114 includes a plurality of lens elements, the object plane of the micro lens array 115 is located among the plurality of lens elements, but the disclosure is not limited thereto.

FIG. 14 is a schematic view of an imaging module 11D according to a fourth embodiment of the disclosure. FIG. 15 is a schematic view of an example of the imaging module 11D depicted in FIG. 14. Referring to FIG. 14 and FIG. 15, an object plane (represented as an object place OP6, for example) of the micro lens array 115 may be located in the third lens assembly 114, and the second portion light beam BP2 may form a virtual image on the object plane (represented as the object place OP6, for example) of the micro lens array 115. In detail, the third lens assembly 114 may include a plurality of lens elements, the object plane of the micro lens array 115 is located among the plurality of lens elements, but the disclosure is not limited thereto.

In the embodiments of the disclosure, the light beams having various fields of view are received by using the micro lens array to reconstruct the 3D image (the first three-dimensional image generated by the second image sensor), and the resolution of the reconstructed 3D image is enhanced by using the 2D image (the two-dimensional image) generated by the first image sensor, such that the 3D image (the second three-dimensional image) having a higher resolution is obtained. The 3D image which may be formed without using dual endoscope lens assemblies is potential for miniaturization of the endoscope diameter. Moreover, as the 3D image is capable of presenting depth and distance information, a surgeon, when performing a fine surgery, is able to perform spatially positioning more accurately, so as to improve surgery accuracy, shorten an operation duration and reduce the risk of surgery.

In some embodiments, imaging areas on the first image sensor and the second image sensor may be the same or different. In some embodiments, the imaging area on the second image sensor may be smaller than the imaging area on the first image sensor.

In some embodiments, the endoscope stereo imaging device meeting 1.21F<D1<1.5F or 0.4F<D1<0.84F has an ideal optical resolution and aberration. In some embodiments, the endoscope stereo imaging device meeting −8.78F<D2<−3.76F or 0.75F<D2<5.03F has an ideal optical resolution and aberration.

In some embodiments, focal lengths of the second lens assembly and the third lens assembly may be the same or different. In some embodiments, the first lens assembly and the second lens assembly may generate distortion opposite to that of the endoscope lens assembly 10, such that total distortion of the two-dimensional image formed on the first image sensor is <30%. In some embodiments, the first lens assembly and the third lens assembly may generate distortion opposite to that of the endoscope lens assembly 10, such that total distortion of the first three-dimensional image formed on the second image sensor is <30%. In some embodiments, a difference between the total distortion of the two-dimensional image and that of the first three-dimensional image is less than ±1%, which is in favor of the enhancement of the resolution of the three-dimensional image.

In some embodiments, the EFL of the micro lens array is greater than 0. In some embodiments, a magnification of the micro lens array is within a range from 0.166 to 0.5, i.e., 0.166≤the magnification of the micro lens array ≤0.5. When the magnification of the micro lens array is more than 0.5, it is difficult to form the 3D image due to insufficient field of view information. On the other hand, when the magnification of the micro lens array is less than 0.166, the spatial resolution of the reconstructed 3D image is too low, which causes difficulty in subsequent image processing (the step of enhancing the resolution of the 3D image).

In some embodiments, the endoscope stereo imaging device can switch the 2D image and the 3D image (the second three-dimensional image having the higher resolution). In some embodiments, from the third lens assembly to the micro lens array, an included angle between a chief ray of the second portion light beam and the optical axis is increased as the field of view is increased. In some embodiments, from the third lens assembly to the micro lens array, the chief ray of the second portion light beam and the optical axis are parallel or nearly parallel to each other (i.e., the included angle between the chief ray and the optical axis is close to 0 degree), such that the micro lens array is consistent in the magnification for the light beams having different fields of view to avoid the difficulty in the subsequent image processing due to too large magnification. A deviation tolerancehe of the included angle between the chief ray and the optical axis is related to the magnification of the micro lens array and other optical design parameters, which will not be particularly limited herein. In some embodiments, the light beams having different fields of view are consistent in numerical apertures (NA) at the image side of the third lens assembly, such that locations and areas of the plurality of sub light beams projected to the second image sensor are in line with preset values to avoid difficulty in the subsequent image processing due to deviations of the locations and areas.

It will be apparent to those skilled in the art that various modifications and variations can be made to the structure of the disclosed embodiments without departing from the scope or spirit of the disclosure. In view of the foregoing, it is intended that the disclosure cover modifications and variations of this disclosure provided they fall within the scope of the following claims and their equivalents.

What is claimed is:

1. An endoscope stereo imaging device, comprising:
an endoscope lens assembly, configured to receive and transmit a light beam; and
an imaging module, disposed on a transmission path of the light beam and comprising a first lens assembly, a beam splitter, a second lens assembly, a first image sensor, a third lens assembly, a micro lens array and a second image sensor, wherein the light beam from the endoscope lens assembly is transmitted to the beam splitter after passing through the first lens assembly and is split into a first portion and a second portion light beams, the first portion light beam is transmitted to the first image sensor via the second lens assembly and forms a two-dimensional image, and the second portion light beam is transmitted to the second image sensor via the third lens assembly and the micro lens array sequentially and forms a first three-dimensional image, wherein the micro lens array disperses the second portion light beam at respective fields of view into a plurality of sub light beams, and the sub light beams respectively form images at different locations of the second image sensor to form the first three-dimensional image, and wherein a distance between a most convex point of an image side surface of the micro lens array and the second image sensor is D1, an effective focal length of the micro lens array is F, and the endoscope stereo imaging device meets $1.21F<D1<1.5F$ or $0.4F<D1<0.84F$.

2. The endoscope stereo imaging device according to claim 1, further comprising: a processor, coupled to the first image sensor and the second image sensor, wherein the processor generates a second three-dimensional image according to the two-dimensional image and the first three-dimensional image, and a resolution of the second three-dimensional image is higher than a resolution of the first three-dimensional image.

3. The endoscope stereo imaging device according to claim 1, wherein a distance between an object plane of the micro lens array and a most convex point of an object side surface of the micro lens array is D2, an effective focal length of the micro lens array is F, and the endoscope stereo imaging device meets $-8.78F<D2<-3.76F$ or $0.75F<D2<5.03F$.

4. The endoscope stereo imaging device according to claim 1, wherein an object plane of the micro lens array is located between the third lens assembly and the micro lens array or at a side of the micro lens array which is far away from the third lens assembly.

5. The endoscope stereo imaging device according to claim 4, wherein the light beam passing through the first lens assembly forms a real image between the first lens assembly and the second lens assembly or between the first lens assembly and the third lens assembly.

6. The endoscope stereo imaging device according to claim 1, wherein an object plane of the micro lens array is located in the third lens assembly, and the second portion light beam forms a real image or a virtual image on the object plane of the micro lens array.

7. The endoscope stereo imaging device according to claim 1, wherein an effective focal length of the micro lens array is greater than 0.

8. The endoscope stereo imaging device according to claim 1, wherein one of an object side surface and an image side surface of the micro lens array is a convex micro lens array surface.

9. The endoscope stereo imaging device according to claim 1, wherein a magnification of the micro lens array is within a range from 0.166 to 0.5.

10. The endoscope stereo imaging device according to claim 1, wherein light beams having different filed of views are consistent in numerical apertures at an image side of the third lens assembly.

11. The endoscope stereo imaging device according to claim 1, wherein imaging areas on the first image sensor and the second image sensor are the same.

12. The endoscope stereo imaging device according to claim 1, wherein an imaging area on the second image sensor is smaller than an imaging area on the first image sensor.

* * * * *